(12) United States Patent
Chen et al.

(10) Patent No.: US 12,285,169 B2
(45) Date of Patent: Apr. 29, 2025

(54) ELECTRIC ENDOSCOPIC STAPLER (71) Applicant: Ningbo Verykind Medical Device Co., Ltd., Zhejiang (CN)

(72) Inventors: Zaihong Chen, Zhejiang (CN); Songbiao Xue, Zhejiang (CN); Weiguo Fu, Zhejiang (CN)

(73) Assignee: Ningbo Verykind Medical Device Co., Ltd., Ningbo (CN)

( * ) Notice: Subject to any disclaimer, the term of this patent is extended or adjusted under 35 U.S.C. 154(b) by 0 days.

(21) Appl. No.: 18/577,924

(22) PCT Filed: Jul. 8, 2022

(86) PCT No.: PCT/CN2022/104552
§ 371 (c)(1),
(2) Date: Jan. 9, 2024

(87) PCT Pub. No.: WO2022/237918
PCT Pub. Date: Nov. 17, 2022

(65) Prior Publication Data
US 2025/0072894 A1    Mar. 6, 2025

(30) Foreign Application Priority Data
May 10, 2021  (CN) .......................... 202110503531.2

(51) Int. Cl.
*A61B 17/072*  (2006.01)
*A61B 17/00*  (2006.01)
(52) U.S. Cl.
CPC ................. *A61B 17/07207* (2013.01); *A61B 2017/00398* (2013.01)
(58) Field of Classification Search
CPC .... A61B 17/07207; A61B 2017/00398; A61B 2017/2927
See application file for complete search history.

(56) References Cited

U.S. PATENT DOCUMENTS

| 2017/0296170 A1 | 10/2017 | Shelton, IV et al. |
| 2019/0038282 A1* | 2/2019 | Shelton, IV ..... A61B 17/07207 |
| 2019/0249759 A1* | 8/2019 | Abbott ..................... F16H 21/44 |

FOREIGN PATENT DOCUMENTS

| CN | 107693066 A | 2/2018 |
| CN | 107693068 A | 2/2018 |

(Continued)

OTHER PUBLICATIONS

International Search Report of PCT/CN2022/104552.
Written Opinion of PCT/CN2022/104552.

*Primary Examiner* — Nathaniel C Chukwurah (57) ABSTRACT

The present disclosure relates to the technical field of endoscopic staplers, in particular to an electric endoscopic stapler, including a housing, a driving motor, a linkage mechanism, a rotating mechanism, and an execution joint; the driving motor being disposed of in the housing; the linkage mechanism including a linkage assembly and a connecting rod, the linkage assembly is driven by and connected to an output shaft of the driving motor, the linkage assembly is connected to one end of the connecting rod, and the linkage assembly being used for converting rotating motion of the driving motor into linear motion of the connecting rod; and the rotating mechanism is connected to the other end of the connecting rod, the execution joint being connected to the rotating mechanism, and the rotating mechanism being used for converting the linear motion of the connecting rod into an angular rotation of the execution joint.

20 Claims, 6 Drawing Sheets

(56) References Cited

FOREIGN PATENT DOCUMENTS

| | | |
|---|---|---|
| CN | 110693553 A | 1/2020 |
| CN | 111588432 A | 8/2020 |
| CN | 112535506 A | 3/2021 |
| CN | 113100858 A | 7/2021 |
| CN | 216724639 U | 6/2022 |

\* cited by examiner

ELECTRIC ENDOSCOPIC STAPLER

CROSS-REFERENCE TO RELATED APPLICATIONS

This application is a national stage application of PCT/CN2022/104552. This application claims priorities from PCT application No. PCT/CN2022/104552, filed Jul. 8, 2022, and from the Chinese patent application 202110503531.2 filed May 10, 2021, the content of which are incorporated herein in the entirety by reference.

TECHNICAL FIELD

The present disclosure relates to the technical field of endoscopic staplers, in particular to an electric endoscopic stapler.

BACKGROUND ART

As one of important instruments for endoscopic surgery, an endoscopic stapler replaces traditional manual suturing and uses titanium nails to amputate or anastomose tissues, thereby being simple, convenient and rapid in operation and greatly shortening the surgical time. Moreover, by using the endoscopic stapler, anastomosis that is narrow in surgical field, deeper in position and difficult in manual operation becomes easy and accurate. Therefore, the endoscopic stapler has become an increasingly important surgical medical instrument.

The stapler needs to be precisely matched and anastomosed with a lesion, and therefore, a joint end of the stapler is required to be subjected to angle adjustment in a limited space, however, most of existing staplers have no angle adjusting structures. The stapler can only be operated manually even if it has an angle adjusting function, and therefore, the precision of angle adjustment is relatively poor.

SUMMARY

In order to solve at least one aspect of the above-mentioned technical problems to a certain extent, the present disclosure provides an electric endoscopic stapler, including a housing, a driving motor, a linkage mechanism, a rotating mechanism, and an execution joint; the driving motor being disposed in the housing; the linkage mechanism including a linkage assembly and a connecting rod, the linkage assembly being driven by and connected to an output shaft of the driving motor, the linkage assembly being connected to one end of the connecting rod, and the linkage assembly being used for converting rotating motion of the driving motor into linear motion of the connecting rod; and the rotating mechanism being connected to the other end of the connecting rod, the execution joint being connected to the rotating mechanism, and the rotating mechanism being used for converting the linear motion of the connecting rod into an angular rotation of the execution joint.

According to the present disclosure, the driving motor is adopted to control the connecting rod to stretch in a linear direction by means of the linkage assembly, and then, the angular rotation of the execution joint is controlled, so that automatic angle adjustment of the execution joint can be achieved, the precision of angle adjustment of the execution joint is higher, and it can be ensured that the execution joint is more precisely aligned to a lesion.

Optionally, the linkage assembly includes a screw rod and a connecting part, the screw rod is driven by and connected to the driving motor, the outer wall of the screw rod is provided with screw threads, one end of the connecting part is spirally connected to the screw rod, and the other end of the connecting part is connected to the connecting rod. The driving motor may drive the screw rod to rotate. Since the connecting part is spirally connected to the screw rod, when the screw rod rotates, the connecting part may be driven to move in the direction of the shaft axis of the screw rod, the connecting part is connected to the screw rod, and therefore, the connecting part can drive the connecting rod to linearly move. The linkage assembly is simple in structure and low in cost.

Optionally, the linkage assembly further includes a linkage nut, the connecting part is provided with a limiting slot, the linkage nut is located in the limiting slot, and the linkage nut sleeves the outer wall of the screw rod and is spirally connected to the screw rod.

The connecting part includes a first connecting part, a second connecting part, a middle connecting part, and springs; the first connecting part is spirally connected to the screw rod, the second connecting part is connected to the connecting rod, a first clamping slot is disposed in the bottom of the first connecting part, a second clamping slot is disposed in the top of the second connecting part, the top of the middle connecting part is located in the first clamping slot, and the bottom of the middle connecting part is located in the second clamping slot; and the springs are disposed between the middle connecting part and the bottom of the second clamping slot, an insertion hole is disposed in the first connecting part, the middle connecting part is provided with a pressing part corresponding to the insertion hole, and the housing is provided with a manual adjusting hole corresponding to the insertion hole. When the driving motor is faulted, a rod-shaped object may be used to sequentially extend into the manual adjusting hole and the insertion hole, and the pressing part is downwards pressed, so that the top of the middle connecting part is out of the first clamping slot, and then, the first connecting part is disconnected to the second connecting part. Moreover, the rod-shaped object is operated to move back and forth in the motion direction of the connecting rod, and thus, the manual angle adjustment of the execution joint can be achieved. By this design, not only can the reset problem of the connecting rod after the driving motor is faulted be solved, but also the execution joint can be manually operated to rotate under some urgent situations.

Optionally, an avoidance slot is disposed in the bottom of the middle connecting part, guide posts extending to the second clamping slot are disposed in the avoidance slot, and the springs sleeve outer walls of the guide posts. On one hand, the compression and stretching directions of the springs can be guided, and on the other hand, effects of protecting and supporting the springs can be achieved.

Optionally, the linkage assembly includes a linkage rack and a transmission gear set, the transmission gear set includes at least one transmission gear, the linkage rack is connected to the connecting rod, the transmission gear is meshed and connected with the linkage rack, and the transmission gear is driven by and connected to the output shaft of the driving motor. The driving motor drives the transmission gear to rotate, when the transmission gears rotate, the linkage rack linearly moves to drive the connecting rod to linearly move, so that the rotating motion of the driving motor is converted into the linear motion of the connecting rod.

Optionally, the connecting part or the linkage rack is provided with a connector, a connecting hole is disposed in one end of the connecting rod, and the connector extends into the connecting hole.

Optionally, the electric endoscopic stapler further includes a speed-reducing gear set, the speed-reducing gear set comprises a plurality of speed-reducing gears, the speed-reducing gear set is driven by and connected to the output shaft of the driving motor, and the linkage assembly is connected to the speed-reducing gear set.

Optionally, the housing includes a fixed housing and a rotary housing, the rotary housing sleeves the fixed housing, the inner wall of the rotary housing is provided with a convex ring, the outer wall of the fixed housing is provided with a limiting ring slot, the convex ring is clamped in the limiting ring slot and is adapted to rotate relative to the limiting ring slot, and the driving motor and the linkage mechanism are both connected to the rotary housing.

Optionally, the electric endoscopic stapler further includes an inner frame, rotating sleeves, and a mounting ring frame, the inner frame is fixedly connected to the fixed housing, the mounting ring frame is fixedly connected to the inner frame, the rotating sleeves sleeve the outer wall of the mounting ring frame and are adapted to rotate relative to the mounting ring frame, and the driving motor is electrically connected to the rotating sleeves.

DESCRIPTION FOR NUMERALS IN THE ACCOMPANYING DRAWINGS

1—housing; 11—rotary housing; 111—manual adjusting hole; 112—convex ring; 113—upper limiting plate; 114—lower limiting plate; 12—fixed housing; 121—limiting ring slot; 13—inner frame; 15—mounting ring frame; 16—rotating sleeve; 17—conductive pillar; 18—electrode tip; 2—execution joint; 3—connecting rod; 4—driving motor; 41—auxiliary mounting frame; 51—screw rod; 52—connecting part; 521—first connecting part; 5211—first fitting part; 522—second connecting part; 5221—insertion hole; 5222—second fitting part; 523—middle connecting part; 5231—pressing part; 5232—avoidance slot; 5233—guide post; 524—limiting slot; 525—first clamping slot; 526—second clamping slot; 528—spring; 53—linkage nut; 55—transmission gear; 56—connector; 57—linkage rack; 6—speed-reducing gear set; 71—rotating rack; 72—first rotating gear; 73—second rotating gear; 8—ejector sleeve; and 81—stroke tabletop.

DETAILED DESCRIPTION OF THE INVENTION

In order to make the above-mentioned objectives, features, and advantages of the present disclosure more obvious and comprehensible, specific embodiments of the present disclosure will be listed below in conjunction with the accompanying drawings.

In addition, in the accompanying drawings of the description of the present disclosure, a forward direction of X represents an advancing direction of a connecting rod, a reverse direction of X represents a retreating direction of the connecting rod; a forward direction of Y represents the right of the connecting rod, a reverse direction of Y represents the left of the connecting rod; and a forward direction of Z represents "above", a reverse direction of Z represents "below".

If there is description related to "first", "second", etc. in embodiments of the present disclosure, the description for "first", "second", etc. is only for descriptive purposes, and cannot be understood as indicating or implying the relative importance or implicitly indicating the number of indicated technical features.

As shown in FIG. 1 to FIG. 3 and FIG. 7, an embodiment of the present disclosure provides an electric endoscopic stapler. The electric endoscopic stapler includes a housing 1, an ejector sleeve 8, a driving motor 4, a linkage mechanism, a rotating mechanism, and an execution joint 2. The housing 1 is provided with a hollow accommodating cavity, and the driving motor 4 is disposed in the accommodating cavity of the housing 1.

The linkage mechanism includes a linkage assembly and a connecting rod 3. The linkage assembly is driven by and connected to an output shaft of the driving motor 4. The ejector sleeve 8 is connected between the housing 1 and the execution joint 2, and the connecting rod 3 is disposed in the ejector sleeve 8. One end of the connecting rod 3 is connected to the linkage assembly, the other end of the connecting rod 3 is connected to the rotating mechanism, and the rotating mechanism is connected to the execution joint 2. The linkage assembly is used for converting rotating motion of the driving motor 4 into linear motion of the connecting rod 3, and the rotating mechanism is used for converting the linear motion of the connecting rod 3 into an angular rotation of the execution joint 2.

When the driving motor 4 rotates, the linkage assembly pulls the connecting rod 3 to linearly move in an extension direction of the ejector sleeve 8, the connecting rod 3 drives the rotating mechanism to run, and the rotating mechanism pulls the execution joint 2 to perform angular transformation.

In the present embodiment, the driving motor is adopted to drive the execution joint 2 to perform angular rotation, which facilitates automatically controlling the angle adjustment of the execution joint 2 and ensures higher precision of angle adjustment of the execution joint 2, so that the execution joint 2 is more precisely aligned to a lesion.

Figure 3:
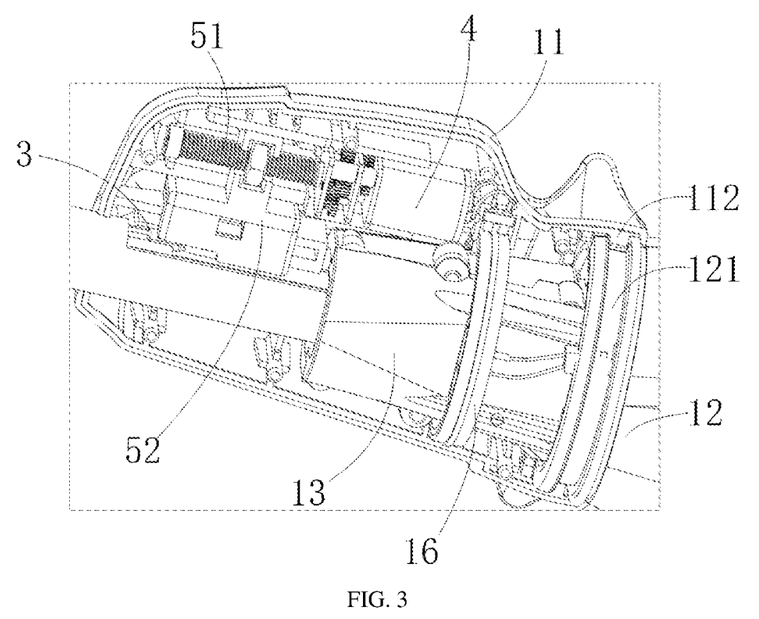
FIG. 3 is a partial enlarged diagram of part A in FIG. 2.
Figure 4:
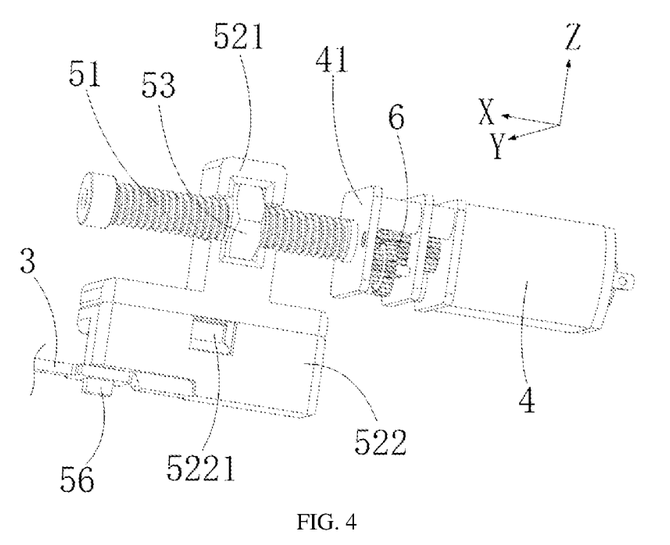
FIG. 4 is a diagram showing a connected structure between a linkage assembly and each of a driving motor and a connecting rod in an embodiment of the present disclosure.

Specifically, as shown in FIG. 3 and FIG. 4, the linkage assembly includes a screw rod 51 and a connecting part 52. The outer wall of the screw rod 51 is provided with screw threads, and the screw rod 51 is parallel to the connecting rod 3. One end of the screw rod 51 is driven by and connected to the driving motor 4, and the other end of the screw rod 51 is rotatably connected to the housing 1 or suspended. A shaft axis of the output shaft of the driving motor 4 is parallel to a shaft axis of the screw rod 51, and the driving motor 4 may drive the screw rod 51 to rotate. One end of the connecting part 52 is spirally connected to the screw rod 51, and the other end of the connecting part 52 is connected to the connecting rod 3. Since the connecting part 52 is spirally connected to the screw rod 51, when the screw rod 51 rotates, the connecting part 52 moves in the direction of the shaft axis of the screw rod 51, the connecting part 52 is spirally connected to the screw rod 51, and therefore, the connecting rod 3 may be driven to linearly move, that is, the shaft axis of the screw rod 51 is parallel to a motion direction of the connecting rod 3. Thus, the rotating motion of the driving motor 4 can be converted into the linear motion of the connecting rod 3. The designed structure is simple, the cost is low, and influences of disposing the driving motor 4 and the linkage assembly on the external diameter of the housing can be reduced as much as possible.

As shown in FIG. 4 to FIG. 7, preferably, the connecting part 52 includes a first connecting part 521 and a second connecting part 522 which recline to each other. The top of the first connecting part 521 is connected to the screw rod 51, and the bottom of the second connecting part 522 is connected to the connecting rod 3. The first connecting part 521 is connected to the second connecting part 522 by a middle connecting part 523, so that the first connecting part 521 can drive the second connecting part 522 to move.

Specifically, a limiting slot 524 is disposed in the top of the first connecting part 521, and openings or through holes allowing the screw rod 51 to penetrate are disposed in front and rear side walls of the limiting slot 524. A linkage nut 53 is disposed in the limiting slot 524, that is, the linkage nut 52 is clamped in the limiting slot 524, and the linkage nut 53 sleeves the outer wall of the screw rod 51 and is spirally connected to the screw rod 51. Optionally, the linkage nut 53 is an ordinary external hexagonal nut. By connecting the connecting part 52 to the screw rod 51 by adopting the linkage nut 53, the cost is low, and the processing difficulty of the first connecting part 521 is simplified.

The bottom end surface of the first connecting part 521 clings and reclines to the top end surface of the second connecting part 522. A first clamping slot 525 upwards recessed is disposed in the bottom end surface of the first connecting part 521. A second clamping slot 526 which is downwards recessed is disposed in the top end surface of the second connecting part 522, and the first clamping slot 525 corresponds to the first clamping slot 525 up and down.

Figure 6:
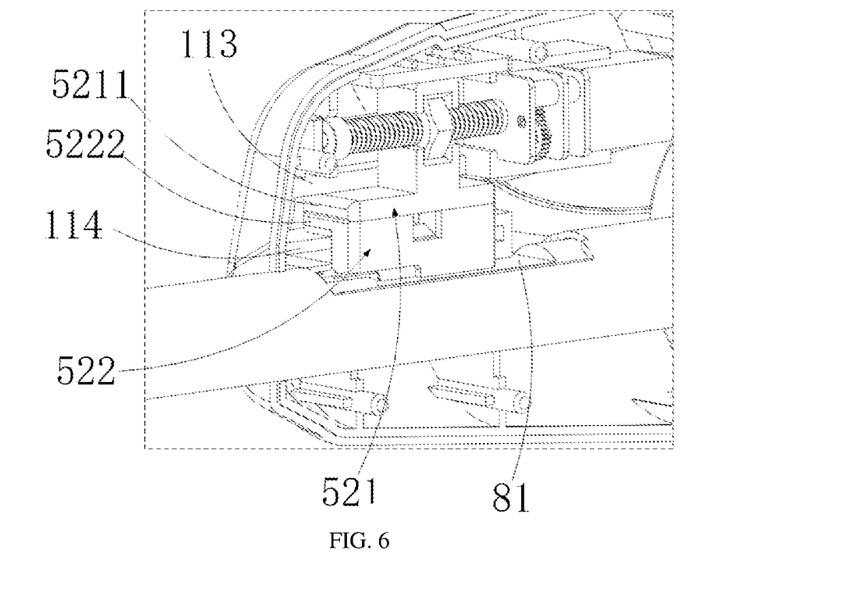
FIG. 6 is a diagram showing a positional relationship among an upper limiting plate, a lower limiting plate and a connecting part in an embodiment of the present disclosure.

The middle connecting part 523 is disposed in a cavity buckled by the second clamping slot 526 and the first clamping slot 525, that is, the top of the middle connecting part 523 is located in the first clamping slot 525, and the bottom of the middle connecting part 523 is located in the second clamping slot 526. Due to the limitation of an inner wall structure of the housing 1, the first connecting part 521 reclines to the second connecting part 522, and therefore, the connection between the first connecting part 521 and the second connecting part 522 can be achieved by the middle connecting part 523. Exemplarily, as shown in FIG. 6, the inner wall of the housing 1 is provided with an upper limiting plate 113 and a lower limiting plate 114 which are parallel to each other. The side wall of the first connecting part 521 is provided with a first fitting part 5211, the side wall of the second connecting part 522 is provided with a second fitting part 5222, the first fitting part 5211 reclines and fits to the second fitting part 5222, and the first fitting part 5211 and the second fitting part 5222 are located between the upper limiting plate 113 and the lower limiting plate 114 and are limited by the upper limiting plate 113 and the lower limiting plate 114.

Figure 5:
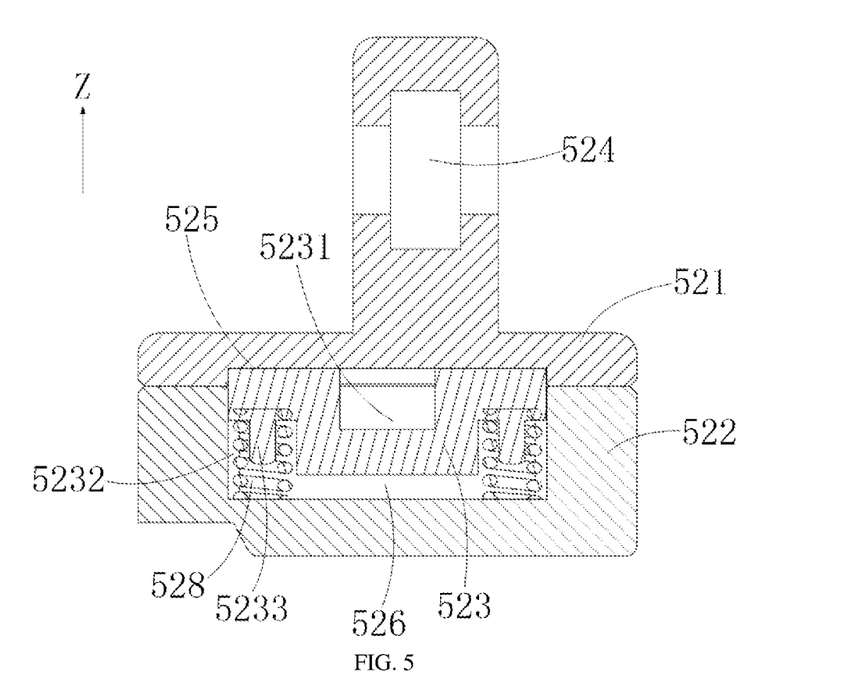
FIG. 5 is schematic diagram of a connecting part in an embodiment of the present disclosure.

Springs 528 are disposed between the middle connecting part 523 and the bottom of the second clamping slot 526, tops of the springs 528 are in contact with the bottom end surface of the middle connecting part 523, and bottoms of the springs 528 are in contact with the bottom of the second clamping slot 526. An insertion hole 5221 is disposed in the side wall of the second connecting part 522, and the insertion hole 5221 is a through hole penetrating through the outer wall of the second connecting part 522 to the middle connecting part 523. The middle connecting part 523 is provided with a pressing part 5231 corresponding to the insertion hole 5221. The pressing part 5231 may be a recess in the side wall of the middle connecting part 523 or a recess in the top surface of the middle connecting part 523. The housing 1 is provided with a manual adjusting hole 111 corresponding to the insertion hole 5221. The manual adjusting hole 111 is a strip-shaped through hole extending along the motion direction of the connecting rod 3.

When the driving motor 4 is faulted, a rod-shaped object may be used to sequentially extend into the manual adjusting hole 111 and the insertion hole 5221, and the pressing part 5231 is downwards pressed. The springs are compressed by the middle connecting part 523, so that the top of the middle connecting part 523 is out of the first clamping slot 525, and then, the first connecting part 521 is disconnected to the second connecting part 522. Then, the rod-shaped object is operated to move back and forth in the motion direction of the connecting rod 3, and thus, the manual angle adjustment and reset for the execution joint can be achieved. By this design, not only can the reset problem of the connecting rod 3 after the driving motor 4 is faulted be solved, but also the execution joint 2 can be manually operated to rotate under some urgent situations. The rod-shaped object in the present embodiment may be a specially-designed manual reset tool, at least one end of the manual reset tool may extend into the manual adjusting hole 111 and the insertion hole 5221 and be matched with the pressing part 5231; and the rod-shaped object may also be any rod-shaped object capable of pressing the pressing part 5231.

Optionally, an avoidance slot 5232 is disposed in the bottom end surface of the middle connecting part 523, guide posts 5233 extending to the second clamping slot 526 are disposed in the avoidance slot 5232, and the springs 528 sleeve outer walls of the guide posts 5223. Due to the arrangement of the avoidance slot 5232 and the guide posts 5223, on one hand, compression and stretching directions of the springs 528 can be guided, and on the other hand, effects of protecting and supporting the springs 528 can be achieved.

Figure 8:
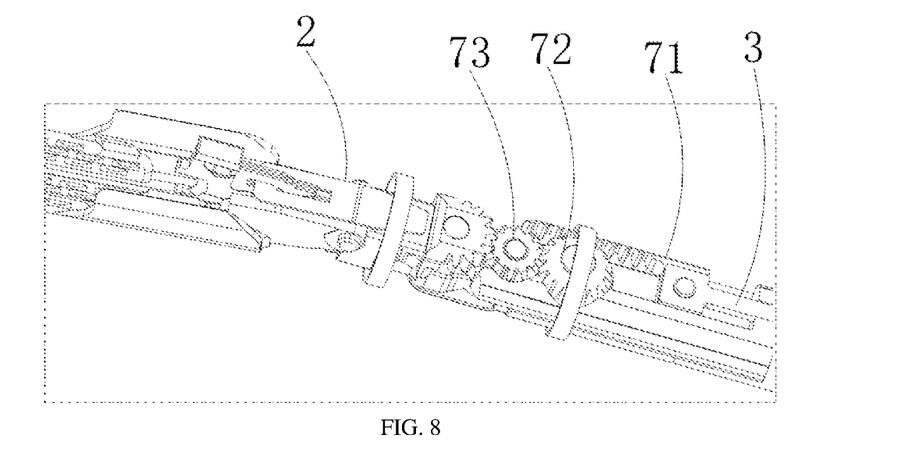
FIG. 8 is a partial enlarged diagram of part B in FIG. 2.

As shown in FIG. 8, optionally, the rotating mechanism includes a rotating rack 71, a first rotating gear 72, and a second rotating gear 73. The rotating rack 71 is meshed and connected to the end of the connecting rod 3, the first rotating gear 72 is meshed and connected to the rotating rack 71, the second rotating gear 73 is meshed and connected to the first rotating gear 72, and an end of the execution joint 2 is meshed and connected to the second rotating gear 73. When linearly moving, the connecting rod 3 pulls the rotating rack 71 to linearly move, the rotating rack 71 drives the first rotating gear 72 to rotate, the first rotating gear 72 drives the second rotating gear 73 to rotate, the second rotating gear 73 drives the execution joint 2 to rotate within a certain angle range, and thus, the angle adjustment of the execution joint 2 is achieved. Of course, the number of the rotating gears is not limited to two, there may be more or one under some conditions.

Figure 9:
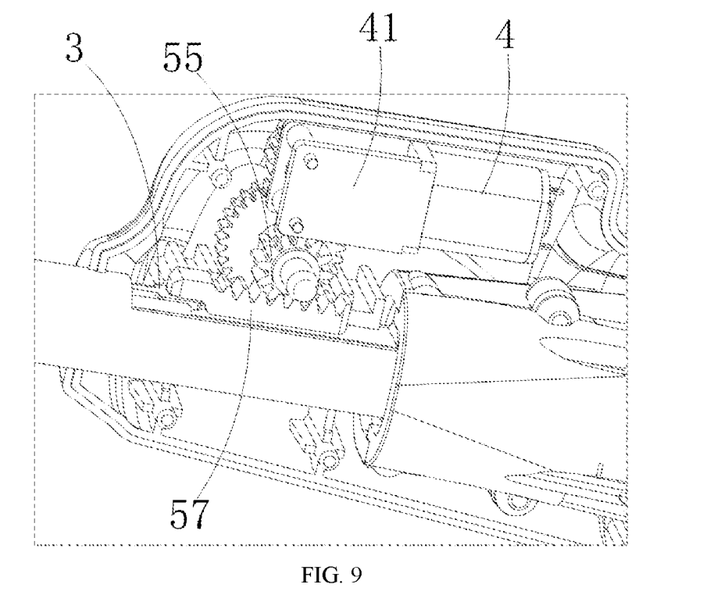
FIG. 9 is a structural diagram of a linkage assembly and a driving motor in another embodiment of the present disclosure.
Figure 10:
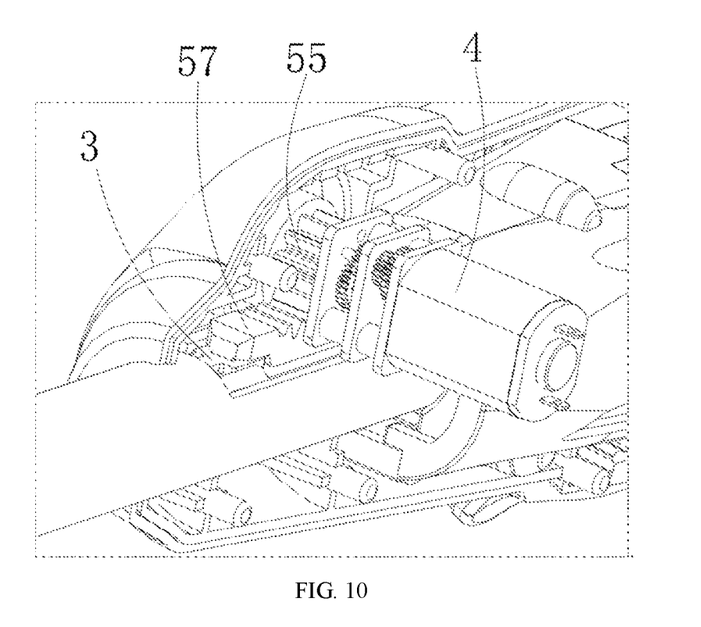
FIG. 10 is a structural diagram of a linkage assembly and a driving motor in further embodiment of the present disclosure.

As shown in FIG. 9 and FIG. 10, in other embodiments, the linkage assembly includes a linkage rack 57 and a transmission gear set. The transmission gear set includes at least one transmission gear 55, and the transmission gear 55 is driven by and connected to the output shaft of the driving motor 4. The linkage rack 57 is meshed and connected to the transmission gear 55.

The linkage rack 57 is connected to the connecting rod 3, and the linkage rack 57 is disposed in parallel to the connecting rod 3. The driving motor 4 drives the transmission gear 55 to rotate, the transmission gear 55 drives the linkage rack 57 to linearly move, the linkage rack 57 drives the connecting rod 3 to linearly move, and thus, the angle adjustment of the execution joint 2 can also be achieved.

Specifically, in the embodiments in FIG. 9, a shaft axis of the transmission gear 55 is vertical to the output shaft of the driving motor 4, and the transmission gear 55 may be driven by and connected to the driving motor 4 by means of two bevel gears which are meshed to each other. In an embodiment in FIG. 10, the shaft axis of the transmission gear 55 is parallel to the output shaft of the driving motor 4. A position where the driving motor 4 is disposed directly affects the external structure and size of the housing 1, and therefore, the position where the driving motor 4 is disposed can be changed according to specific use requirements of the electric endoscopic stapler. Moreover, the number of the transmission gear 55 is not limited to be one, and may be more.

On the basis of the above-mentioned embodiment, as shown in FIG. 4 and FIG. 6, the ejector sleeve 8 is provided with a stroke tabletop 81, and the bottom end surface of the connecting part 52 moves on the stroke tabletop. The bottom end surface of the connecting part 52 is provided with a connector 56, a connecting hole is disposed in one end of the connecting rod 3, and the connector 56 extends into the connecting hole. Due to the existence of the stroke tabletop 81, it is ensured that the connector 56 cannot be separated from the connecting rod 3.

Similarly, the bottom end surface of the linkage rack 57 is also provided with a connector 56, a connecting hole is disposed in the end of the connecting rod 3, and the connector 56 extends into the connecting hole 31.

Preferably, as shown in FIG. 4, a speed-reducing gear set 6 is driven by and connected to the output end of the driving motor 4, the speed-reducing gear set 6 includes a plurality of speed-reducing gears, and the two adjacent speed-reducing gears are meshed and connected to each other. The speed-reducing gears are mounted on an auxiliary mounting frame 41, and the auxiliary mounting frame 41 is connected to the housing 1. The linkage assembly is connected to the speed-reducing gear set 6. By disposing the speed-reducing gear set 6, the driving torsion and speed change function of the linkage assembly can be improved.

Figure 1:
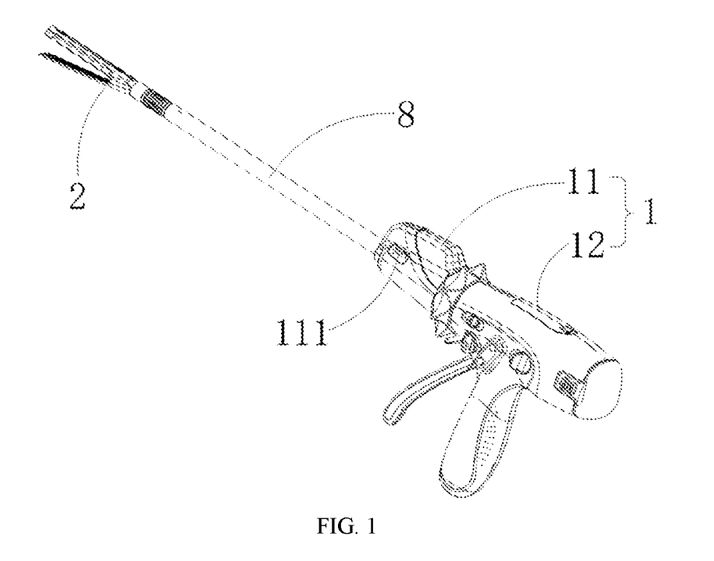
FIG. 1 is a diagram showing an external structure of an electric endoscopic stapler in an embodiment of the present disclosure.
Figure 2:
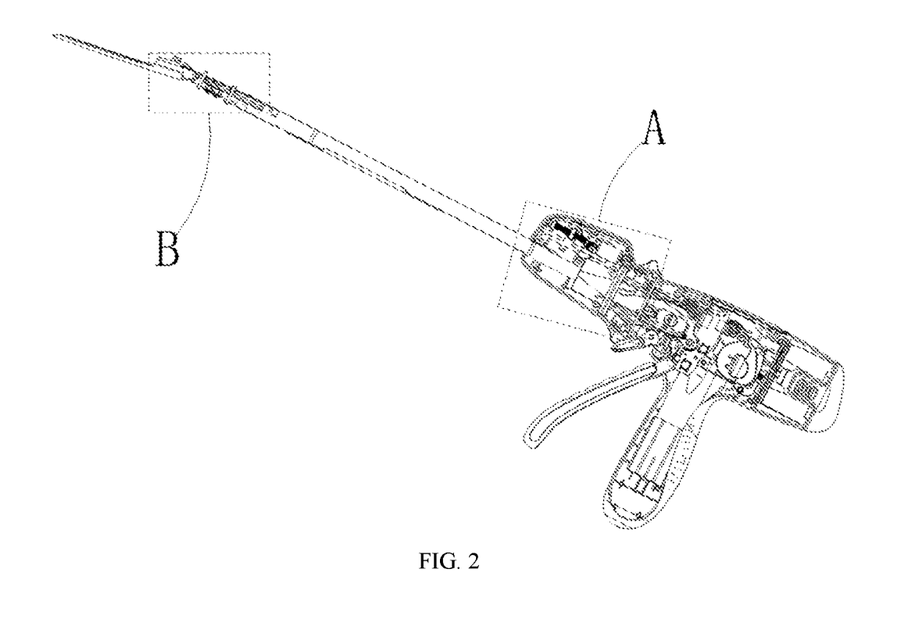
FIG. 2 is a diagram showing a partial internal structure of an electric endoscopic stapler in an embodiment of the present disclosure.
Figure 7:
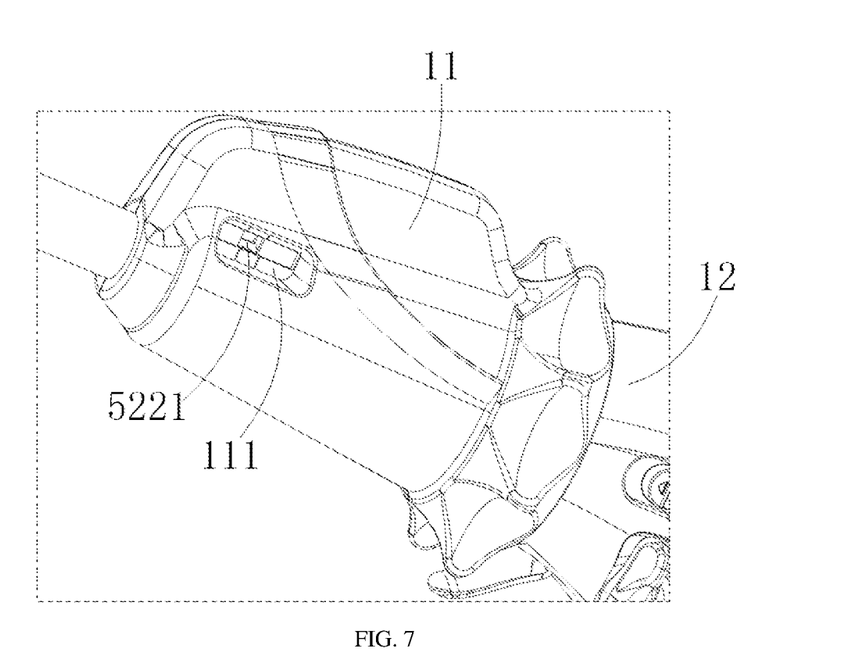
FIG. 7 is a diagram showing an external structure of a rotary housing in an embodiment of the present disclosure.

Preferably, as shown in FIG. 1, FIG. 3 and FIG. 7, the housing 1 includes a fixed housing 12 and a rotary housing 11, and the rotary housing 11 sleeves the outer wall on one end of the fixed housing 12. The inner wall of the rotary housing 11 is provided with a convex ring 112, the outer wall of the fixed housing 12 is provided with a limiting ring slot 121, and the convex ring 112 is clamped in the limiting ring slot 121 and is adapted to rotate relative to the limiting ring slot 121. The outer wall of the rotary housing 11 is provided with a plurality of operation ridges, and the operation ridges are distributed in the circumferential direction of the outer wall of the rotary housing 11, and thus, it is convenient to rotate the rotary housing 11 by hand. The ejector sleeve 8, the driving motor 4 and the linkage mechanism are all fixedly connected to the rotary housing 11. Therefore, the rotation of the ejector sleeve 8 can be achieved by rotating the rotary housing 11, then, the rotation of the execution joint 2 around the axis of the ejector sleeve 8 is achieved, at the same time, the driving motor 4 can also drive the angle adjustment of the execution joint 2 within a certain plane, and therefore, the multidirectional position adjustment of the execution joint 2 can be ensured, and it can be ensured that the execution joint 2 is precisely aligned to a lesion.

Figure 11:
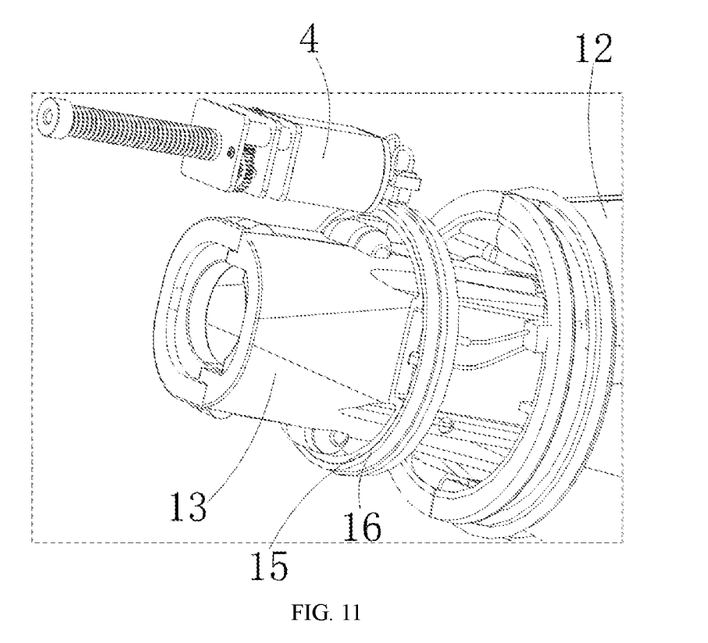
FIG. 11 is a diagram showing a connection relationship between each of rotating sleeves and a driving motor in an embodiment of the present disclosure.
Figure 12:
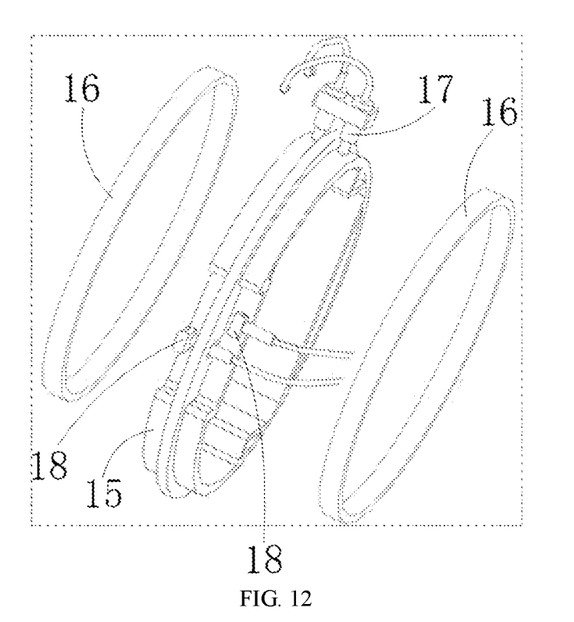
FIG. 12 is a structural diagram of each of rotating sleeves and a mounting ring frame in an embodiment of the present disclosure.

Preferably, as shown in FIG. 11 and FIG. 12, an inner frame 13 and a mounting ring frame 15 are disposed in the fixed housing 12. The inner frame 13 is fixedly connected to the fixed housing 12, the mounting ring frame 15 sleeves the inner frame 13, and the inner wall of the mounting ring frame 15 is fixedly connected to the outer wall of the inner frame 13.

The annular outer wall of the mounting ring frame 15 is sleeved with rotating sleeves 16, and the rotating sleeves 16 are capable of rotating relative to the mounting ring frame 15. There are two coaxially-disposed rotating sleeves 16, the outer wall of the mounting ring frame 15 is provided with a circle of insulated bulges, and the insulated bulges are blocked between the two rotating sleeves 16. The driving motor 4 is connected to a wire connector, and each of two conductive pillars 17 on two electrodes of the wire connector is connected to one of the rotating sleeves 16. Two electrode tips 18 are respectively disposed on two sides of the insulated bulges of the mounting ring frame 15, and each of the electrode tips 18 is used to be in contact with one of the rotating sleeves 16 so as to achieve electric connection. The electrode tips 18 is connected to a control system or a power supply system.

In this way, the power supply of the driving motor 4 is not affected even if the rotary housing 11 rotates. It is ensured that the rotation and angle adjustment of the execution joint 2 can be operated at the same time.

Although the present disclosure is disclosed as above, the protection scope of the present disclosure is not limited thereto. Those skilled in the art can make various changes and modifications without departing from the spirit and scope of the present disclosure, and all these changes and modifications will fall within the protection scope of the present disclosure.

The invention claimed is:

1. An electric endoscopic stapler, comprising a housing (1), a driving motor (4), a linkage mechanism, a rotating mechanism, and an execution joint (2);

the driving motor (4) being disposed in the housing (1);
the linkage mechanism comprising a linkage assembly and a connecting rod (3), the linkage assembly being driven by and connected to an output shaft of the driving motor (4), the linkage assembly being connected to one end of the connecting rod (3), and the linkage assembly being used for converting rotating motion of the driving motor (4) into linear motion of the connecting rod (3); and the rotating mechanism being connected to the other end of the connecting rod (3), the execution joint (2) being connected to the rotating mechanism, and the rotating mechanism being used for converting the linear motion of the connecting rod (3) into an angular rotation of the execution joint (2).

2. The electric endoscopic stapler according to claim 1, wherein the linkage assembly comprises a screw rod (51) and a connecting part (52), the screw rod (51) is driven by and connected to the driving motor (4), an outer wall of the screw rod (51) is provided with screw threads, one end of the connecting part (52) is spirally connected to the screw rod (51), and the other end of the connecting part (52) is connected to the connecting rod (3).

3. The electric endoscopic stapler according to claim 2, wherein the linkage assembly further comprises a linkage nut (53), the connecting part (52) is provided with a limiting slot (524), the linkage nut (53) is clamped in the limiting slot (524), and the linkage nut (53) sleeves the outer wall of the screw rod (51) and is spirally connected to the screw rod (51).

4. The electric endoscopic stapler according to claim 3, further comprising a speed-reducing gear set (6), the speed-reducing gear set (6) comprising a plurality of speed-reducing gears, the speed-reducing gear set (6) being driven by and connected to the output shaft of the driving motor (4), and the linkage assembly being connected to the speed-reducing gear set (6).

5. The electric endoscopic stapler according to claim 3, wherein the housing (1) comprises a fixed housing (12) and a rotary housing (11), the rotary housing (11) sleeves the fixed housing (12), the inner wall of the rotary housing (11) is provided with a convex ring (112), the outer wall of the fixed housing (12) is provided with a limiting ring slot (121), the convex ring (112) is clamped in the limiting ring slot (121) and is adapted to rotate relative to the limiting ring slot (121), and the driving motor (4) and the linkage mechanism are both connected to the rotary housing (11).

6. The electric endoscopic stapler according to claim 2, wherein the connecting part (52) comprises a first connecting part (521), a second connecting part (522), a middle connecting part (523), and springs (528);

the first connecting part (521) is spirally connected to the screw rod (51), the second connecting part (522) is connected to the connecting rod (3), a first clamping slot (525) is disposed in the bottom of the first connecting part (521), a second clamping slot (526) is disposed in the top of the second connecting part (522), the top of the middle connecting part (523) is located in the first clamping slot (525), and the bottom of the middle connecting part (523) is located in the second clamping slot (526); and the springs (528) are disposed between the middle connecting part (523) and the bottom of the second clamping slot (526), an insertion hole (5221) is disposed in the first connecting part (521), the middle connecting part (523) is provided with a pressing part (5231) corresponding to the insertion hole (5221), and the housing (1) is provided with a manual adjusting hole (111) corresponding to the insertion hole (5221).

7. The electric endoscopic stapler according to claim 6, wherein an avoidance slot (5232) is disposed in the bottom of the middle connecting part (523), guide posts (5233) extending to the second clamping slot (526) are disposed in the avoidance slot (5232), and the springs (528) sleeve outer walls of the guide posts (5233).

8. The electric endoscopic stapler according to claim 7, further comprising a speed-reducing gear set (6), the speed-reducing gear set (6) comprising a plurality of speed-reducing gears, the speed-reducing gear set (6) being driven by and connected to the output shaft of the driving motor (4), and the linkage assembly being connected to the speed-reducing gear set (6).

9. The electric endoscopic stapler according to claim 7, wherein the housing (1) comprises a fixed housing (12) and a rotary housing (11), the rotary housing (11) sleeves the fixed housing (12), the inner wall of the rotary housing (11) is provided with a convex ring (112), the outer wall of the fixed housing (12) is provided with a limiting ring slot (121), the convex ring (112) is clamped in the limiting ring slot (121) and is adapted to rotate relative to the limiting ring slot (121), and the driving motor (4) and the linkage mechanism are both connected to the rotary housing (11).

10. The electric endoscopic stapler according to claim 6, further comprising a speed-reducing gear set (6), the speed-reducing gear set (6) comprising a plurality of speed-reducing gears, the speed-reducing gear set (6) being driven by and connected to the output shaft of the driving motor (4), and the linkage assembly being connected to the speed-reducing gear set (6).

11. The electric endoscopic stapler according to claim 6, wherein the housing (1) comprises a fixed housing (12) and a rotary housing (11), the rotary housing (11) sleeves the fixed housing (12), the inner wall of the rotary housing (11) is provided with a convex ring (112), the outer wall of the fixed housing (12) is provided with a limiting ring slot (121), the convex ring (112) is clamped in the limiting ring slot (121) and is adapted to rotate relative to the limiting ring slot (121), and the driving motor (4) and the linkage mechanism are both connected to the rotary housing (11).

12. The electric endoscopic stapler according to claim 2, wherein the connecting part (52) is provided with a connector (56), a connecting hole (31) is disposed in one end of the connecting rod (3), and the connector (56) extends into the connecting hole (31).

13. The electric endoscopic stapler according to claim 2, further comprising a speed-reducing gear set (6), the speed-reducing gear set (6) comprising a plurality of speed-reducing gears, the speed-reducing gear set (6) being driven by and connected to the output shaft of the driving motor (4), and the linkage assembly being connected to the speed-reducing gear set (6).

14. The electric endoscopic stapler according to claim 2, wherein the housing (1) comprises a fixed housing (12) and a rotary housing (11), the rotary housing (11) sleeves the fixed housing (12), the inner wall of the rotary housing (11) is provided with a convex ring (112), the outer wall of the fixed housing (12) is provided with a limiting ring slot (121), the convex ring (112) is clamped in the limiting ring slot (121) and is adapted to rotate relative to the limiting ring slot (121), and the driving motor (4) and the linkage mechanism are both connected to the rotary housing (11).

15. The electric endoscopic stapler according to claim 1, wherein the linkage assembly comprises a linkage rack (57) and a transmission gear set, the transmission gear set comprises at least one transmission gear (55), the linkage rack (57) is connected to the connecting rod (3), the transmission gear (55) is meshed and connected with the linkage rack (57), and the transmission gear (55) is driven by and connected to the output shaft of the driving motor (4).

16. The electric endoscopic stapler according to claim 15, further comprising a speed-reducing gear set (6), the speed-reducing gear set (6) comprising a plurality of speed-reducing gears, the speed-reducing gear set (6) being driven by and connected to the output shaft of the driving motor (4), and the linkage assembly being connected to the speed-reducing gear set (6).

17. The electric endoscopic stapler according to claim 15, wherein the housing (1) comprises a fixed housing (12) and a rotary housing (11), the rotary housing (11) sleeves the fixed housing (12), the inner wall of the rotary housing (11) is provided with a convex ring (112), the outer wall of the fixed housing (12) is provided with a limiting ring slot (121), the convex ring (112) is clamped in the limiting ring slot (121) and is adapted to rotate relative to the limiting ring slot (121), and the driving motor (4) and the linkage mechanism are both connected to the rotary housing (11).

18. The electric endoscopic stapler according to claim 1, further comprising a speed-reducing gear set (6), the speed-reducing gear set (6) comprising a plurality of speed-reducing gears, the speed-reducing gear set (6) being driven by and connected to the output shaft of the driving motor (4), and the linkage assembly being connected to the speed-reducing gear set (6).

19. The electric endoscopic stapler according to claim 1, wherein the housing (1) comprises a fixed housing (12) and a rotary housing (11), the rotary housing (11) sleeves the fixed housing (12), the inner wall of the rotary housing (11) is provided with a convex ring (112), the outer wall of the fixed housing (12) is provided with a limiting ring slot (121), the convex ring (112) is clamped in the limiting ring slot (121) and is adapted to rotate relative to the limiting ring slot (121), and the driving motor (4) and the linkage mechanism are both connected to the rotary housing (11).

20. The electric endoscopic stapler according to claim 19, further comprising an inner frame (13), rotating sleeves (16), and a mounting ring frame (15), the inner frame (13) being fixedly connected to the fixed housing (12), the mounting ring frame (15) being fixedly connected to the inner frame (13), the rotating sleeves (16) sleeving the outer wall of the mounting ring frame (15) and being adapted to rotate relative to the mounting ring frame (15), and the driving motor (4) being electrically connected to the rotating sleeves (16).

\* \* \* \* \*